(12) United States Patent
Borkholder et al.

(10) Patent No.: US 11,020,524 B1
(45) Date of Patent: Jun. 1, 2021

(54) PERISTALTIC MICROPUMPS AND FLUID DELIVERY DEVICES THAT INCORPORATE THEM

(71) Applicants: David A. Borkholder, Canandaigua, NY (US); Farzad Forouzandeh, Rochester, NY (US); Robert Nash Carter, Honeoye Falls, NY (US); Denis Roger Cormier, Pittsford, NY (US); Joseph P. Walton, Tampa, FL (US); Robert Dana Frisina, Tampa, FL (US)

(72) Inventors: David A. Borkholder, Canandaigua, NY (US); Farzad Forouzandeh, Rochester, NY (US); Robert Nash Carter, Honeoye Falls, NY (US); Denis Roger Cormier, Pittsford, NY (US); Joseph P. Walton, Tampa, FL (US); Robert Dana Frisina, Tampa, FL (US)

(73) Assignees: University of South Florida, Tampa, FL (US); Rochester Institute of Technology, Rochester, NY (US)

( * ) Notice: Subject to any disclaimer, the term of this patent is extended or adjusted under 35 U.S.C. 154(b) by 940 days.

(21) Appl. No.: 15/437,356

(22) Filed: Feb. 20, 2017

Related U.S. Application Data (60) Provisional application No. 62/297,221, filed on Feb. 19, 2016.

(51) Int. Cl.
*A61M 5/142* (2006.01)

(52) U.S. Cl.
CPC .... *A61M 5/14276* (2013.01); *A61M 5/14228* (2013.01); *A61M 2005/14208* (2013.01);

(Continued)

(58) Field of Classification Search
CPC ...... A61M 5/14228; A61M 2205/0244; A61M 5/14248; A61M 5/14276; A61M 5/16809;

(Continued)

(56) References Cited

U.S. PATENT DOCUMENTS 6,520,753 B1 2/2003 Grosjean
6,531,417 B2 3/2003 Choi
(Continued)

FOREIGN PATENT DOCUMENTS

WO WO2012048261 A2 4/2012

OTHER PUBLICATIONS

Xu, et al., "Development, characterization, and theoretical evaluation of electroactive polymer-based micropump diaphragm", Science Direct, Elsevier, 2005.

(Continued)

*Primary Examiner* — Manuel A Mendez
(74) *Attorney, Agent, or Firm* — Thomas | Horstemeyer, LLP (57) ABSTRACT

In one embodiment, a peristaltic micropump comprising a substrate having a first side and a second side, a microtube that extends across the first side of the substrate, and multiple pump actuators formed on the first side of the substrate and positioned adjacent to the microtube at discrete, spaced positions along the length of the microtube, wherein the micropump is configured to sequentially actuate the pump actuators so as to create peristaltic action that drives fluid contained in the microtube along the length of the tube.

16 Claims, 7 Drawing Sheets

(52) U.S. Cl.
CPC ............... *A61M 2205/0216* (2013.01); *A61M 2205/0244* (2013.01); *A61M 2205/3368* (2013.01); *A61M 2205/3523* (2013.01); *A61M 2205/3673* (2013.01); *A61M 2205/50* (2013.01); *A61M 2205/8206* (2013.01)

(58) Field of Classification Search
CPC ........ F04B 43/082; F04B 43/12; F04B 43/14; F04B 19/006; F04B 43/046; F04B 43/043; F04B 19/24; F04B 43/06; F16K 99/0001; B01L 3/50273; B01L 3/502738
See application file for complete search history.

(56) References Cited

U.S. PATENT DOCUMENTS

| | | | |
|---|---|---|---|
| 6,589,198 | B1 | 7/2003 | Soltanpour |
| 6,632,400 | B1* | 10/2003 | Brennen ........... B01L 3/502707 204/452 |
| 7,104,768 | B2 | 9/2006 | Richter |
| 7,651,673 | B1 | 1/2010 | Insepov |
| 7,985,057 | B2 | 7/2011 | Haar |
| 8,079,278 | B2 | 12/2011 | Xi |
| 8,080,220 | B2 | 12/2011 | McAvoy |
| 8,353,682 | B2* | 1/2013 | Patrascu ................ F04B 43/06 417/322 |
| 9,091,251 | B1 | 7/2015 | Ullakko |
| 10,065,403 | B2* | 9/2018 | Putnam ................. G01N 21/05 |
| 2002/0071785 | A1 | 6/2002 | Beach |
| 2003/0057391 | A1* | 3/2003 | Krulevitch .......... F16K 99/0011 251/11 |
| 2003/0196900 | A1 | 10/2003 | Chuang |
| 2009/0143761 | A1* | 6/2009 | Cantor .................. A61N 1/325 604/501 |
| 2019/0344057 | A1* | 11/2019 | Cima ................ A61M 5/14276 |

OTHER PUBLICATIONS

Ehrlich, et al., "Experimental characterization of Novel microdiffuser elements", Journal of Physics; conference series 525, 2014.
Pagel, et al., "Microfluidic systems in PCB technology", IEEE, 2005.
Jeong, et al., "Fabrication of peristaltic PDMS micropump", Elsevier, Science Direct, 2005.
Johnson, et al., "Towards an implantable, low flow micropump that uses no power in the blocked-flow state", MDPI, micromachines, 2016.
Chuang, et al., Polydimethylisoxane (PDMS) peristaltic pump characterization for programmable lab-on-a-chip applications, Twelfth International Conference on Miniaturized Systems for Chemistry and Life Sciences, 2008.
Merkel, et al., "A new technology for fluidic microsystems based on PCB technology", Elsevier, Sensors and Actuators 77, 1998.
Solovev, et al., Tunable catalytic tubular micro-pumps operating at low concentrations of hydrogen peroxide; Phys. Chem. Chem. Phys., 2011.
Luque, et al., "Electroosmotic impulsion device for integration in PCB-MEMS", Electron Devices (CDE), 2013.
Lee, et al., "An electrostatically driven valve-less peristaltic micropump with a stepwise chamber", Sensors and Actuators A, 187, 2012.
Thomas, et al., 3-D printed composite microfluidic pump for wearable biomedical applications; Elsevier, Additive Manufacturing 9, 2016.
Wu, et al., "TITAN: a conducing polymer based microfluidic pump", Inst of Physics Publishing, Smart Mater, Strucut. 14, 2005.
Tandon, et al., Microfabricated infuse-withdraw micropump component for an integrated inner-ear drug-delivery platform, Biomed Microdevices, 2015.
Chan, et al., "Simple, cost-effective 3D printed microfluidic components for disposable, point of care colorimetric analysis", ResearchGate, 2015.

* cited by examiner

PERISTALTIC MICROPUMPS AND FLUID DELIVERY DEVICES THAT INCORPORATE THEM

CROSS-REFERENCE TO RELATED APPLICATION

This application claims priority to U.S. Provisional Application Ser. No. 62/297,221, filed Feb. 19, 2016, which is hereby incorporated by reference herein in its entirety.

NOTICE OF GOVERNMENT-SPONSORED RESEARCH

This invention was made with Government support under Grant Number R01DC014568 awarded by the National Institutes of Health. The Government has certain rights in the invention.

BACKGROUND

Biomedical engineering advances in protective and restorative inner ear biotherapies have created new opportunities to address vestibular disorders, deafness, and noise-induced, drug-induced, sensorineural, and age-related hearing loss. To avoid unwanted, systemic side-effects, controllable, programmable drug delivery systems are essential for therapeutic development in animal models, and for future human clinical translation with implantable, subcutaneous or behind-the-ear delivery systems. Rodents offer significant advantages for studies involving specific transgenic, knock-in, and knockout variants that model different human diseases and communication disorders. However, the small size of rodents necessitates key advances in pump miniaturization for implantation, and scaling of flow rates and volumes to match cochlear anatomy.

Microelectromechanical systems (MEMS) micropumps have been proposed for use in situations in which small volumes of liquid are to be delivered from a small device. While MEMS micropumps can be effective in certain applications, it can be difficult to integrate microtubing with a MEMS micropump for purposes of delivering the liquid from the micropump to a target site. It can therefore be appreciated that it would be desirable to have alternative micropumps with which microtubing can be more easily integrated.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have alternative micropumps with which microtubing can be more easily integrated. Disclosed herein are examples of such micropumps. As described below, the micropumps are configured as peristaltic micropumps having integrated microtubes with which liquids, such as drugs and other biotherapeutic compounds, can be delivered from the micropump to a target site, such as a site within an animal or human. In some embodiments, the micropumps comprise multiple pump actuators associated with a microtube. During operation of the micropump, the pump actuators can be activated in a particular sequence so as to drive liquid through the microtube using peristaltic action. In some embodiments, the micropumps are unlike conventional peristaltic pumps typically used in the medical field and, therefore, are configured as non-rotary peristaltic pumps that do not comprise any rotary elements, which simplifies the fabrication of the device on a microscale.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
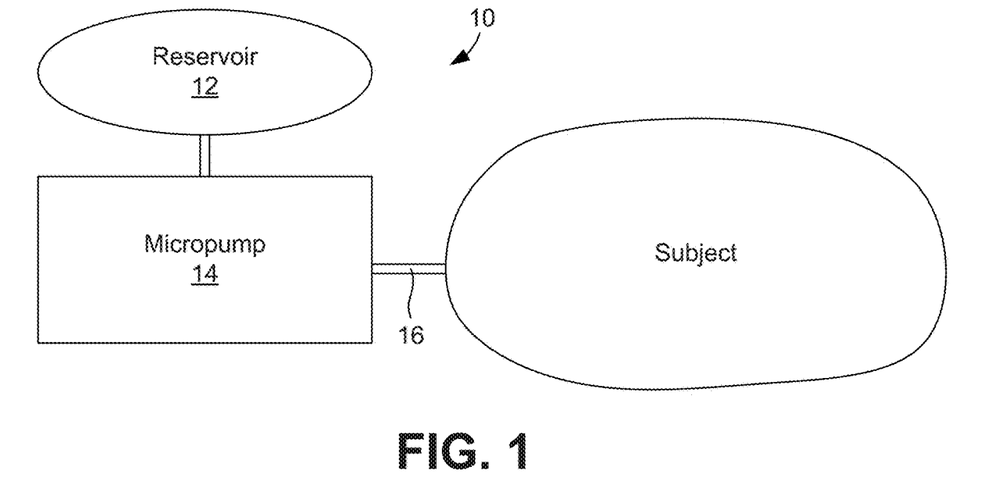
FIG. 1 is a schematic drawing of a fluid delivery device as applied to a subject.

FIG. 1 schematically illustrates a fluid delivery device 10 that can be used to deliver a liquid to a target location. In some embodiments, the fluid delivery device 10 can be configured as a drug delivery device that can be used to deliver drugs to an animal or human subject. The drugs that can be delivered can vary depending upon the application. In other embodiments, the fluid delivery device 10 can be used to deliver other substances to a target area. For example, the device 10 can be used to deliver gene therapy compounds or cells suspended within a liquid to a target area. Irrespective of the application, the fluid delivery device 10 can be said to include a reservoir 12 that can contain the liquid to be delivered and a micropump 14 that can drive the liquid from the reservoir and to a target site within the subject via a microtube 16.

An example embodiment for the micropump 14 is illustrated in FIG. 2. More particularly, FIG. 2 includes multiple sequential views that illustrate an example of fabrication of the micropump 14. Beginning with FIG. 2A, the micropump 14 is constructed on a polymeric substrate 18, which comprises part of a printed circuit board (PCB). The substrate 18 is miniaturized so as to enable subcutaneous implantation of the micropump 14 in animals and/or humans. By way of example, the substrate 18 can be approximately 6 mm to 10 mm long and approximately 6 mm to 10 mm wide.

Figure 2A:
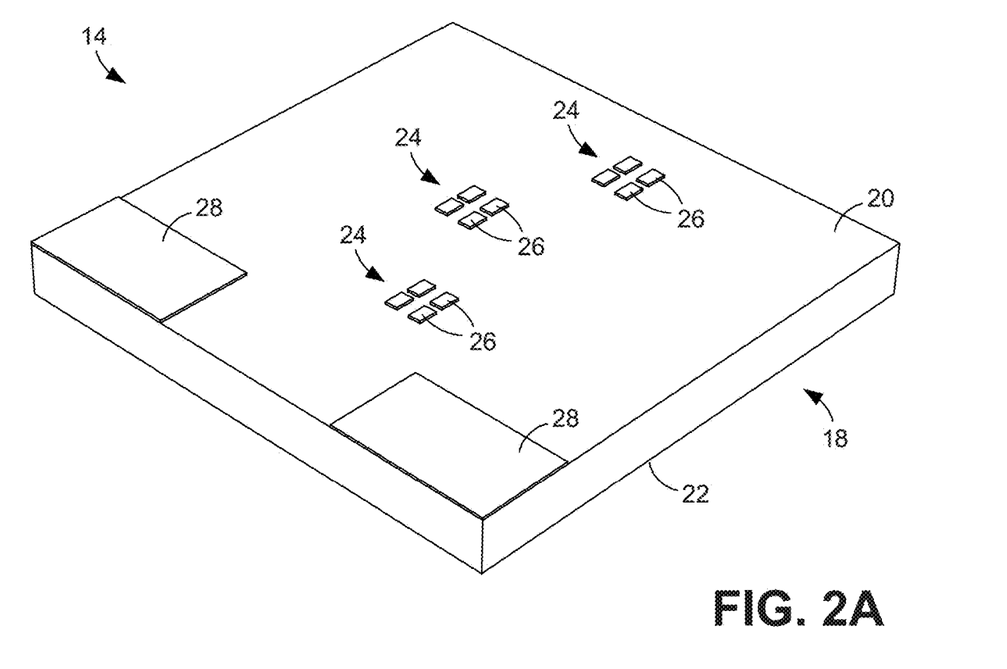
FIGS. 2A-2F are sequential perspective views illustrating the fabrication of an embodiment of a micropump that can be used in the fluid delivery device of FIG. 1.

The substrate 18 comprises a first side having a first surface 20 and a second side having a second surface 22 opposite to the first surface. Which of these surfaces is the "top" or "bottom" of the substrate 18 depends upon the orientation in which the substrate is used. In the embodiment of the liquid delivery device 70 shown in FIGS. 6 and 7 described below, the first surface 20 is the bottom surface and the second surface 22 is the top surface. Provided on the first surface 20 of the substrate 18 are multiple groups 24 of electrical contacts 26. In the illustrated embodiment, three such groups 24 of contacts 26 are provided. In some embodiments, each electrical contact 26 comprises a pad of conductive material that has been deposited on the surface 20 of the substrate 18 using a suitable microfabrication deposition technique, such as three-dimensional (e.g., polymer inkjet) printing. As described below, each group 24 of contacts 26 is associated with an individual pump actuator of the micropump 14. In this example, the micropump 14 comprises three such actuators. It is noted, however, that alternative numbers of pump actuators could be used, if desired. Also shown in FIG. 2A are two additional electrical contacts 28 that can be used to supply power to the micropump 14.

Figure 2B:
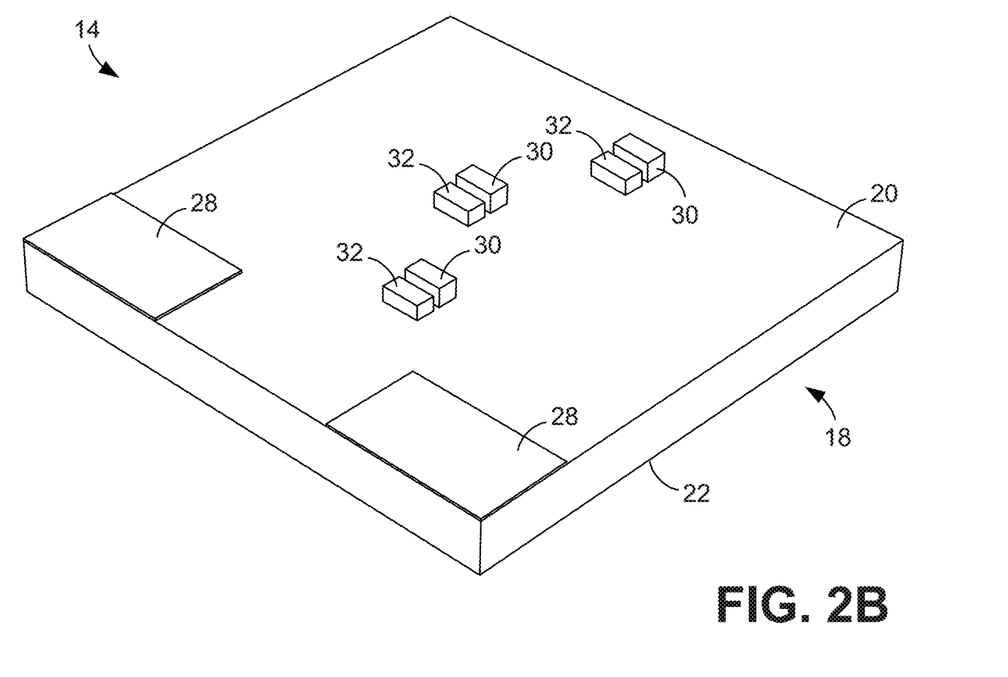

With reference next to FIG. 2B, a heating element 30 and a temperature sensor 32 are mounted to each group 24 of electrical contacts 26. In this embodiment, the heating elements heat an associated actuation member that, when heated, physically changes so as to effect a change in a microtube that is integrated into the micropump 14 (see FIG. 2D). In some embodiments, this physical change is expansion of the actuation member that compresses the microtube so as to locally displace fluid contained within the microtube. The temperature sensors 32 provide an indication of the temperature of the actuation member and, therefore, facilitate closed loop control over the pump actuator. In some embodiments, the heating elements 30 comprise resistors and the temperature sensors 34 comprise thermistors.

Figure 2C:
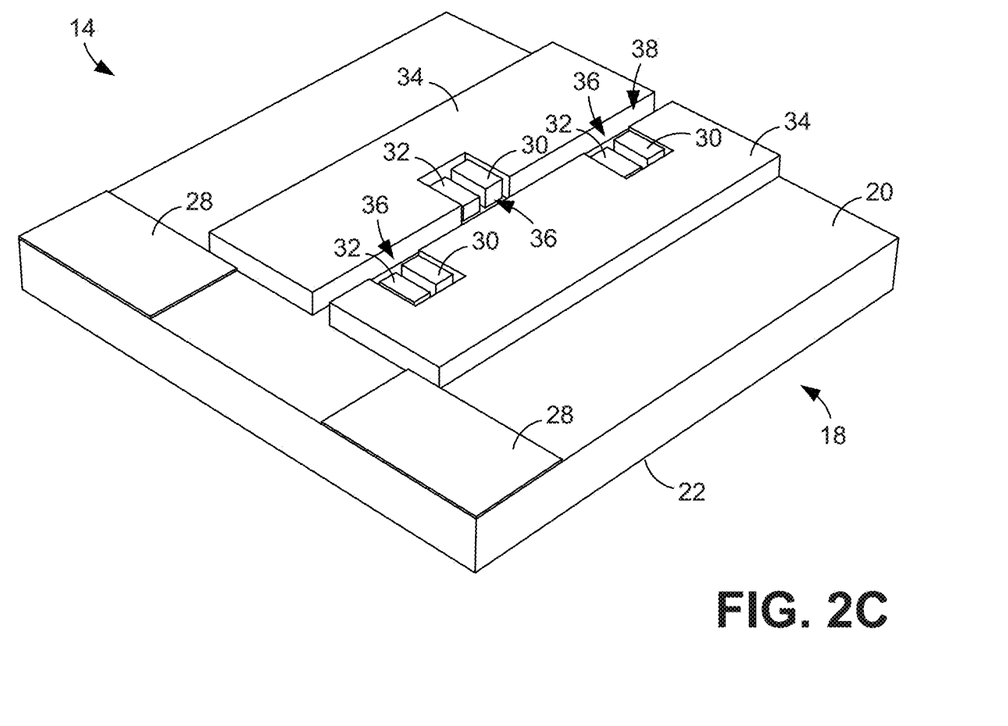

Referring next to FIG. 2C, lateral elements 34 are provided on the surface 20 adjacent to the pairs of heating elements 30 and temperature sensors 32. In some embodiments, the lateral elements 34 are also formed by depositing a polymer material on the surface 20 using a suitable microfabrication deposition technique, such as three-dimensional printing. Together, the lateral elements 34 form the lateral portions of chambers 36 for the pump actuators. These chambers 36 contain the heating elements 30 and the temperature sensors 32 and, as described below, further contain and confine the actuation members.

Figure 2D:
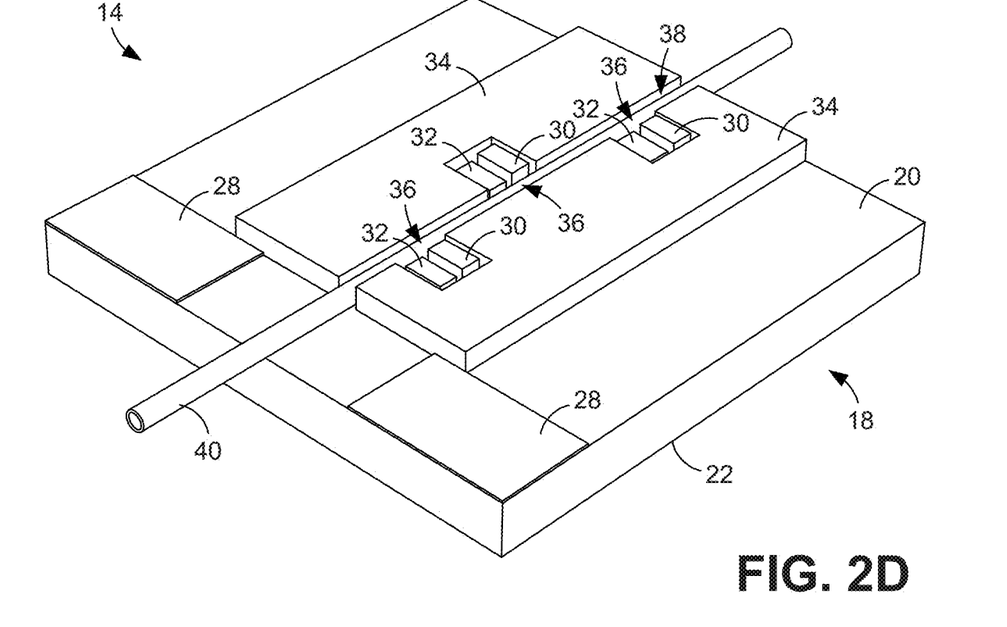

The lateral elements 34 further form an elongated linear channel 38 adapted to receive the microtube upon which the pump actuators will act. A flexible microtube 40 is illustrated positioned within this channel 38 in FIG. 2D and resting upon the substrate surface 20. In some embodiments, the microtube 40 is made of a polymeric material, such as polyurethane. The microtube 40 is small in size so as to also be well suited for implantation. In some embodiments, the microtube 40 has an inner diameter of approximately 1 to 1000 μm. By way of example, the microtube 40 can have an inner diameter of approximately 125 μm and an outer diameter of approximately 250 μm. As indicated in FIG. 2D, when the microtube 40 is positioned within the channel 38, inner lateral walls of the lateral elements 34 are placed in close proximity or in contact with the outer lateral surfaces of the microtube and top surfaces of the lateral elements are positioned at or above the top surface of the microtube. In addition, the pairs of heating elements 30 and temperature sensors 32 are positioned in close proximity to the microtube 40 at discrete, spaced locations along the length of the microtube.

Figure 2E:
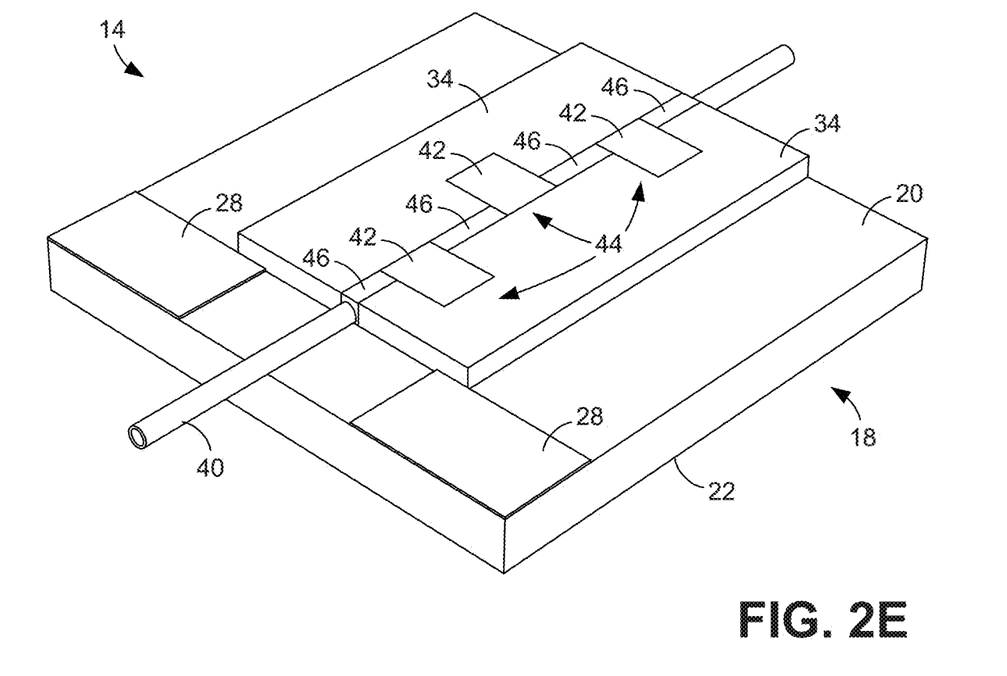

Turning next to FIG. 2E, the pump actuator chambers 36 are shown filled with actuation members 42, forming multiple discrete pump actuators 44. In some embodiments, the actuation members 42 comprise masses of phase-change material that, when heated to their phase-change temperature, change phase and either expand or contract. By way of example, the actuation members 42 can comprise a solid wax, such as paraffin, that, when heated to its melting point, changes phase into a liquid and expands. This expansion compresses the microtube 40 in the location of the pump actuator 44 and, therefore, displaces liquid contained in the microtube at that location. In some embodiments, this phase change can be achieved with as little 6 mW of power. While wax has been identified as one possible phase-change material, other phase-change materials can be used, such as polyethylene glycol (PEG) that also expands when it changes phase to a liquid, or a gallium alloy that expands when it changes phase into a solid.

In alternative embodiments, the actuation member 42 need not be a phase-change material. For instance, the actuation member 42 could be a shape-memory alloy (e.g., nitinol) element that, when heated, changes shape and either directly or indirectly compresses the microtube 40. In an indirect compression example, the shape-memory element can act upon a lever, cam, or other suitable component that directly interfaces with the microtube. It is further noted, that, while the pump actuators 44 have been described as being actuated using heat, it is possible to use other means for actuation. One such means is electricity. For example, the actuation members 42 could comprise volumes of water that undergo hydrolysis, which causes expansion, when an electrical potential is applied. In another example, the pump actuators 44 could instead comprise piezoelectric actuators that are activated using an electrical potential. In still further embodiments, the pump actuators 44 could be actuated using a magnetic field. As can be appreciated from this discussion, the precise nature of the pump actuators 44 is not as critical as the function they serve, which is to locally compress the microtube 40 in a desired sequence.

As is further shown in FIG. 2E, the space that remains in the channel 38 after the microtube 40 has been placed in the channel and the actuation members 42 have been placed in their respective pump actuator chambers 36 can be filled with a suitable filler material 46, such as a UV-cured resin. This material 46 ensures that the microtube 40 remains in position within the channel 38 and prevents migration of the actuator member material in cases in which it changes phase.

Figure 2F:
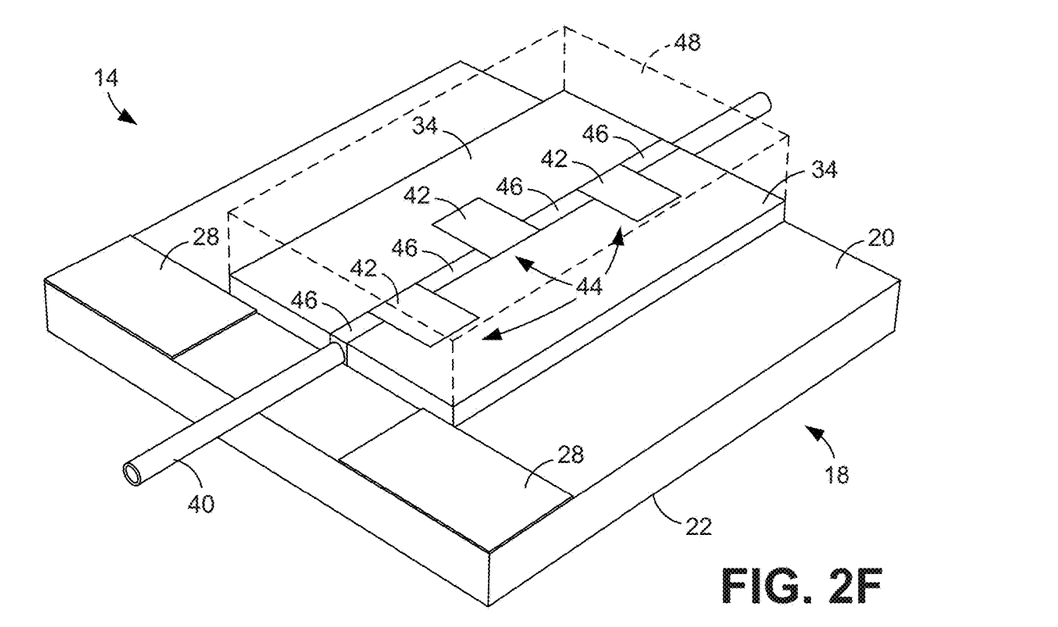

With reference next to FIG. 2F, a top element 48, which can also comprise a UV-cured resin, is provided on top of the lateral elements 34. This top element 48 forms the tops of the pump actuator chambers 36 and the channel 38 so as to confine each of these spaces. It can, therefore, be appreciated that the chambers 36 are defined by the substrate surface 20 on the bottom, the inner walls of the lateral elements 34 on the sides, and the top element 48 on top. While each of these chambers 36 is open to the channel 38, the chambers are closed by the microtube 40 and the filler material 46. It can also be appreciated that the channel 38 is also defined by the substrate surface 20 on the bottom, the inner walls of the lateral elements 34 on the sides, and the top element 48 on top. While discrete portions of the channel 38 at the locations of the chambers 36 are open to the chambers, these portions are closed by the actuation members 42.

Although not illustrated in FIG. 2, the pump actuator chambers 36 can further contain resilient elements that are selected so as to deform to enable greater expansion of the actuation members 42 to avoid situations in which the members can expand to a volume greater than that of their chambers 36. This avoids damage to the chambers 36 and the remainder of the micropump 14. When provided, the resilient elements only deform after full deformation of the microtube 40 is achieved so as not to compromise the operation of the micropump 14.

Figure 3A:
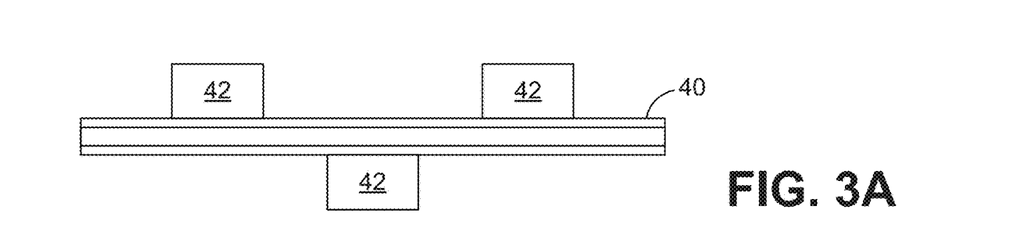
FIGS. 3A-3D are sequential schematic views that illustrate an example of the pumping action that can be produced with the completed micropump of FIG. 2F.
Figure 3B:
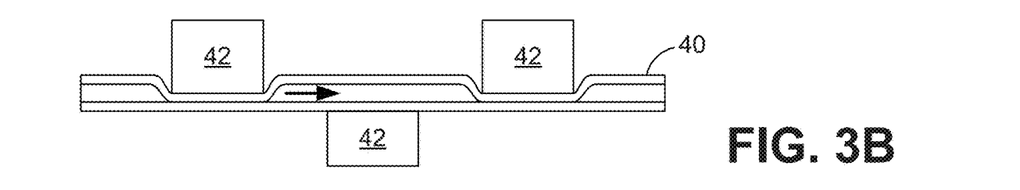

FIGS. 3A-3D illustrate the peristaltic action of the micropump 14. More particularly, FIG. 3 illustrates how sequential actuation (expansion) of the actuation members 42 causes fluid flow through the microtube 40. It is assumed that the microtube 40 contains a fluid to be delivered to a target site under the driving force of the micropump 14. Beginning with FIG. 3A, none of the actuation members 42 has been actuated and there is no fluid flow as a result. In FIG. 3B, the left and right actuation members 42 have been actuated so as to compress the microtube 40 adjacent to the left and right actuation members. As noted above, this actuation can, in some embodiments, comprise expansion of the actuation members 42 due to heating of the members. Regardless, when the left and right actuation members 42 have been actuated, fluid that was adjacent to the left actuation member has been moved to the right, as indicated by the directional arrow.

Figure 3C:
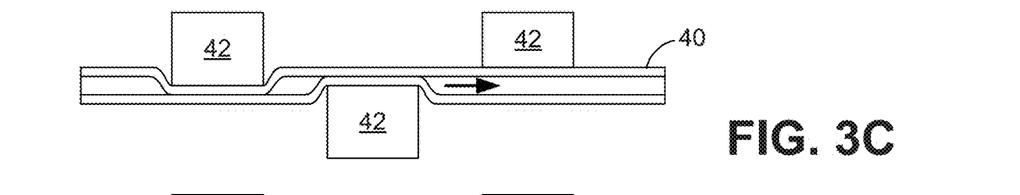
Figure 3D:
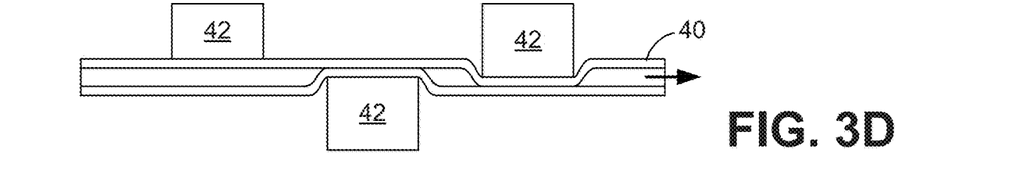

Turning to FIG. 3C, the center actuation member 42 has been actuated and the right actuation member 42 has been de-actuated, while the left actuation member 42 has been left in the actuated position. As indicated by the directional arrow of this figure, this causes the fluid within the microtube 40 to move farther to the right. Finally, with reference to FIG. 3D, the right actuation member 42 has been actuated so as to again move the fluid even farther to the right, as indicated by the directional arrow. As can be appreciated from FIGS. 3A-3D, this sequential actuation of the actuation members 42 creates peristalsis that displaces the fluid along the length of the microtube 40 and, therefore, drives the liquid through the microtube for purposes of delivery to a target site.

Figure 4:
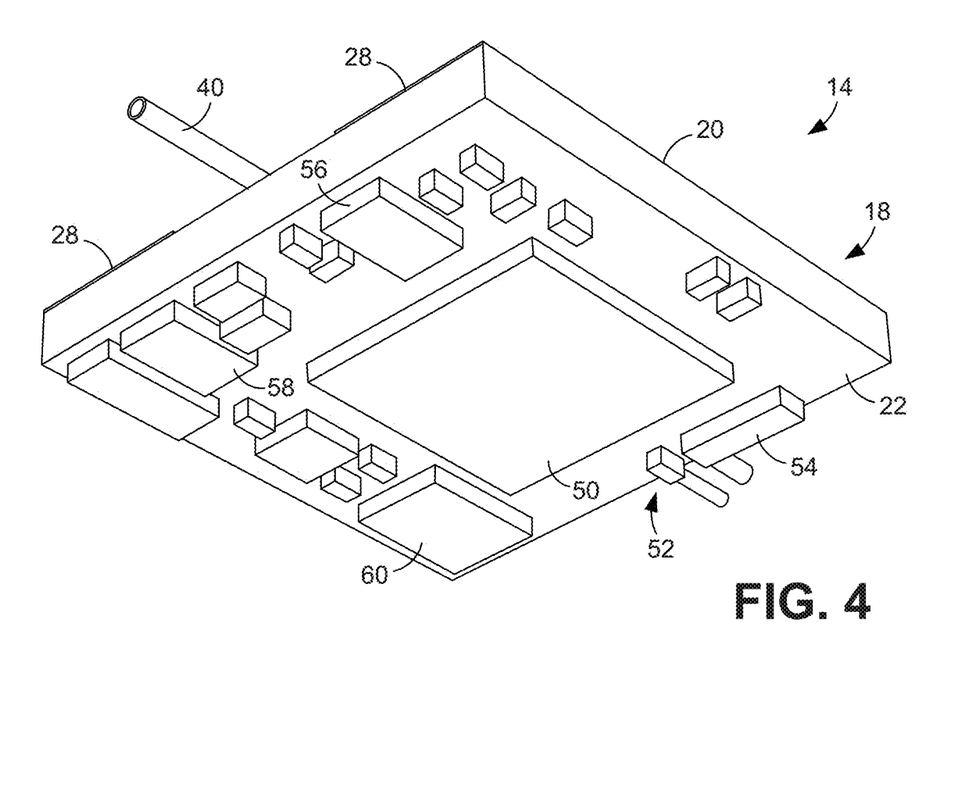
FIG. 4 is a further perspective view the completed micropump of FIG. 2F, illustrating electronic components of the micropump.
Figure 5:
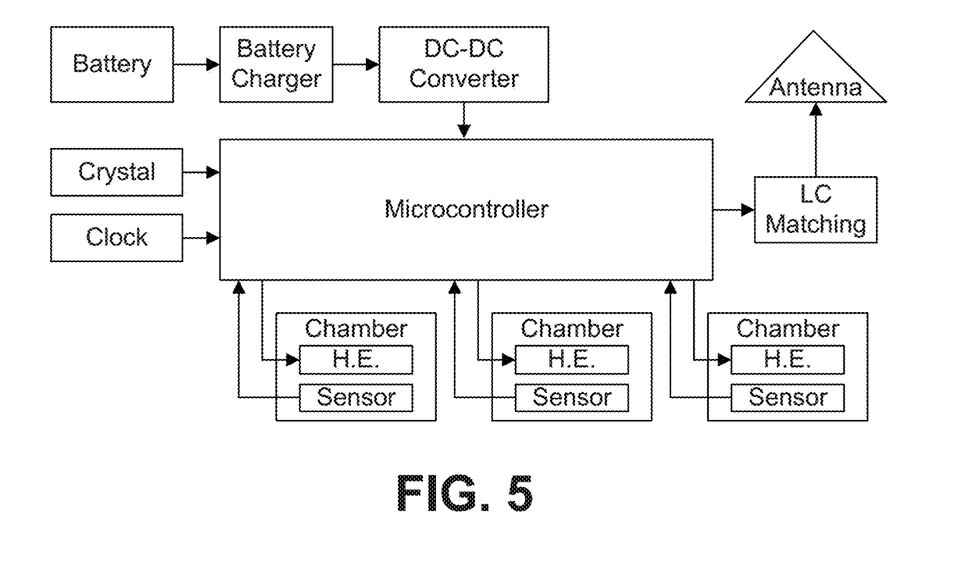
FIG. 5 is an electrical schematic diagram of electronic components of the micropump shown in FIG. 4.

FIG. 4 illustrates the side of the micropump 14 opposite to that shown in FIG. 2. As shown in FIG. 4, various electrical components are mounted to the second surface 22 of the substrate 18 that are used to operate and control the mechanical components provided on the other side of the substrate. As the mechanical components are provided on one side of the substrate 18 and the electrical components are provided on the other side of the substrate, challenges associated with electrical connection between the mechanical and electrical components are avoided and an integrated micropump package comprising all necessary components is achieved. As shown in FIG. 4, the electrical components mounted to the second surface 22 can include a wireless programmable microcontroller 50, an antenna 52 and associated matching network 54, a battery charger 56, a DC-DC converter 58, and a clock and a crystal 60. The electrical connections between these components is illustrated in the electrical schematic diagram of FIG. 5. Also shown in FIG. 5 are a rechargeable battery, such as an inductive rechargeable battery, and electrical connections between the microcontroller and the heating elements and temperature sensors of each pump actuator chamber.

Figure 6:
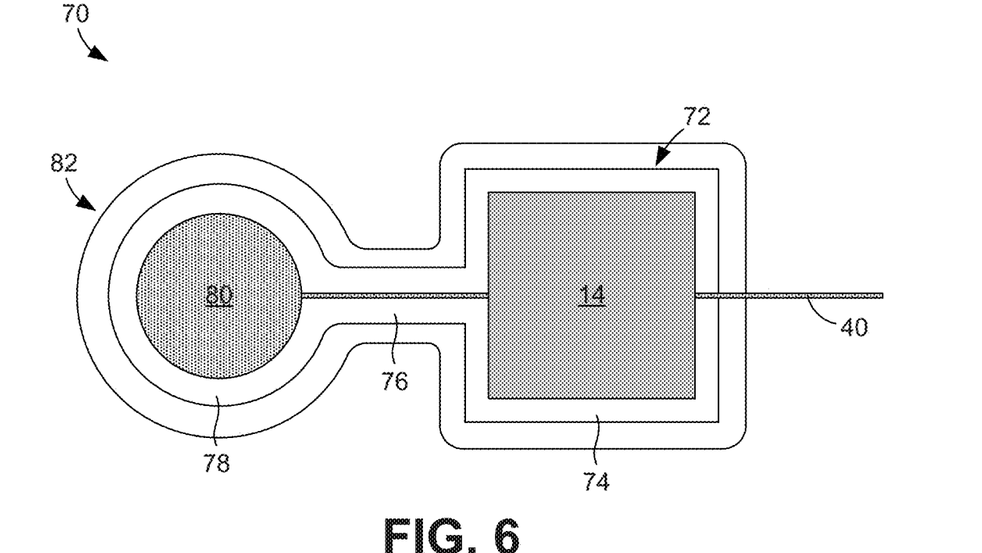
FIG. 6 is a top view of an embodiment of an implantable fluid delivery device that incorporates the completed micropump of FIG. 2F.
Figure 7:
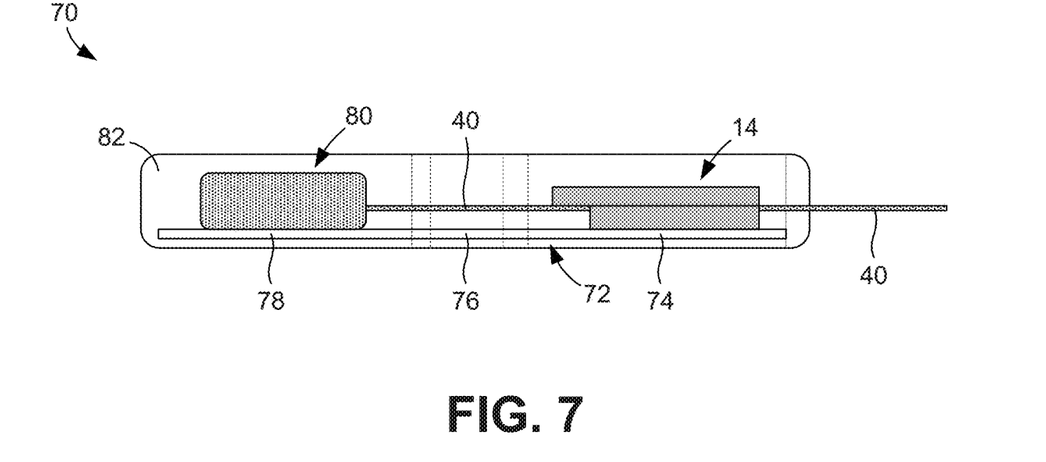
FIG. 7 is a side view of the fluid delivery device of FIG. 6.

As noted above, the micropump 14 can form part of a fluid (e.g., drug) delivery device. FIGS. 6 and 7 illustrate an example embodiment for such a delivery device. In these figures, a fluid delivery device 70 is shown that incorporates the micropump 14. The micropump 14 is shown mounted to a thin base plate 72, which can be made of a polymeric material, such as an acrylic material. In some embodiments, the base plate 72 can form the top element 48 shown in FIG. 2F. The base plate 72 comprises a pump portion 74 that provides support to the micropump 14. Extending from the pump portion 74 of the base plate 72 is a neck portion 76 that extends to a reservoir portion 78 that provides support to a refillable reservoir 80 in which a liquid to be delivered by the device 70 can be contained. As is further shown in FIGS. 6 and 7, the micropump 14 and the base plate 72 are fully encapsulated in a resilient, polymeric encapsulation material 82, such as a silicone material like polydimethylsiloxane (PDMS). This material 82 also forms lateral sides and the top of the reservoir 80, which can be punctured to refill the reservoir 80. As is also shown in the figures, the microtube 40 extends from the micropump 14 to the reservoir 80 so that fluid contained in the reservoir can be drawn from the reservoir and delivered by the micropump to the target site. In some embodiments, both the encapsulation material 82 and the exposed portion of the microtube 40 can be coated with a suitable biocompatible material, such as parylene-C. In some embodiments, the entire liquid delivery device 70 can be approximately 2 to 6 mm thick, approximately 10 to 30 mm long, and approximately 6 to 12 mm wide.

Figure 8:
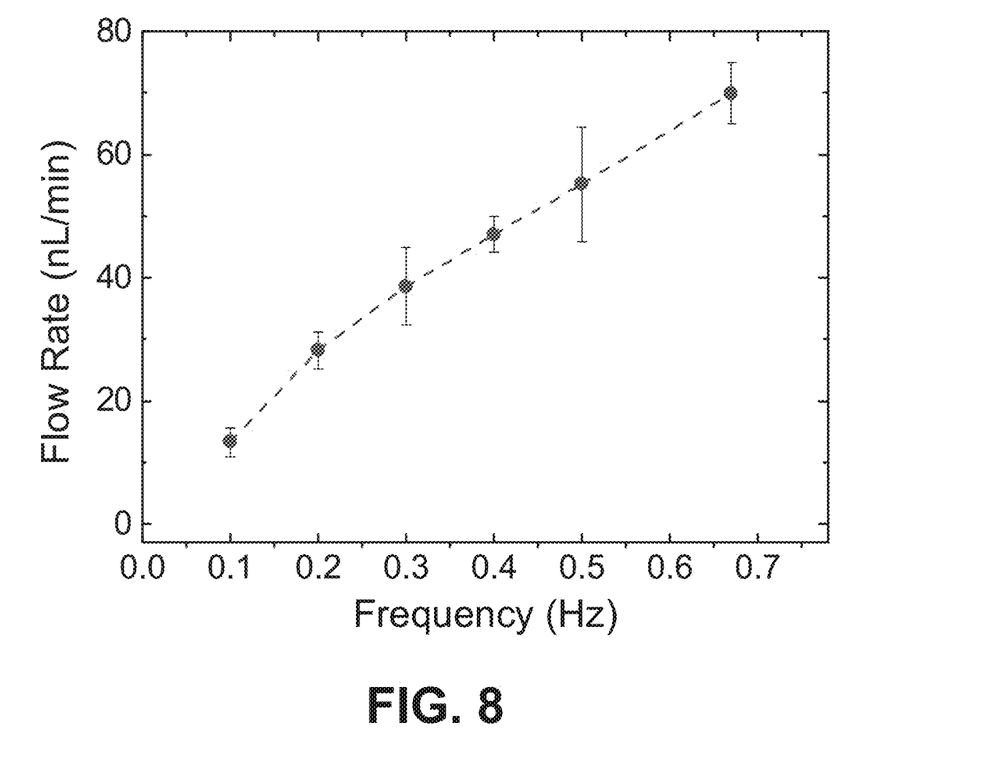
FIG. 8 is a graph that illustrates example flow rates achievable using the micropump of FIG. 2F.

FIG. 8 is a graph that illustrates example flow rates that were observed for a fabricated micropump that was constructed for a rodent intracochlear drug delivery application.

The invention claimed is:

1. A peristaltic micropump comprising:
a substrate having a first side and a second side;
a microtube that extends across the first side of the substrate;
multiple pump actuators formed on the first side of the substrate and positioned adjacent to the microtube at discrete, spaced positions along the length of the microtube, each pump actuator comprising a solid actuation member that is configured to expand when actuated;
wherein the micropump is configured to sequentially actuate the pump actuators so as to cause their actuation members to sequentially expand and sequentially compress the microtube to create peristaltic action that drives fluid contained in the microtube along the length of the microtube; and
one or more electrical contacts located on a surface of the substrate, the one or more electrical contacts used to supply power to the micropump.

2. The micropump of claim 1, wherein the substrate comprises part of a printed circuit board.

3. The micropump of claim 1, wherein an inner diameter of the microtube is no greater than 1000 microns.

4. The micropump of claim 1, wherein each pump actuator comprises a pump actuator chamber that is open to the microtube and that contains the associated actuation member.

5. The micropump of claim 4, wherein each pump actuator chamber and a chamber in which the microtube is provided are formed by the substrate, lateral elements formed on the substrate, and a top element formed on the lateral element.

6. The micropump of claim 1, wherein the actuation members expand when heated.

7. The micropump of claim 6, wherein each pump actuator further comprises a heating element configured to heat its associated actuation member and a temperature sensor configured to measure the temperature of the heating element.

8. The micropump of claim 1, wherein the actuation members are solid masses of phase-change material that change phase and become liquid masses when heated to their melting points, the liquid masses comprising larger volumes than the solid masses.

9. The micropump of claim 1, further comprising a microcontroller provided on the second side of the substrate, the microcontroller being configured to control the sequential actuation of the pump actuators to obtain the peristaltic action.

10. The micropump of claim 1, wherein the actuation members are solid masses of shape-memory alloy.

11. An implantable fluid delivery device comprising:
a reservoir configured to contain a fluid to be delivered to a target site; and
a peristaltic micropump including a printed circuit board having a first side and a second side, a microtube that extends across the first side of the circuit board and to the reservoir, multiple pump actuators formed on the first side of the substrate and positioned adjacent to the microtube at discrete, spaced positions along the length of the microtube, each pump actuator including a solid actuation member that is configured to expand when actuated, and a microcontroller provided on the second side of the circuit board, the microcontroller being configured to control sequential actuation of the pump actuators that causes their actuation members to sequentially expand and sequentially compress the microtube to so as to create peristaltic action that drives the fluid contained in the reservoir along the length of the microtube.

12. The device of claim 11, wherein the reservoir and micropump are encapsulated within a resilient polymeric material.

13. The device of claim 12, wherein the device is approximately 2 to 6 mm thick, approximately 10 to 30 mm long, and approximately 6 to 12 mm wide.

14. The micropump of claim 11, wherein the actuation members expand when heated.

15. The micropump of claim 14, wherein each pump actuator comprises a heating element configured to heat its associated actuation member and a temperature sensor configured to measure the temperature of the heating element.

16. A method for delivering a liquid to a target site within an animal or human subject, the method comprising:
providing a fluid delivery device including a reservoir configured to contain the liquid to be delivered to the target site and a peristaltic micropump including a printed circuit board having a first side and a second side, a microtube that extends across the first side of the circuit board and to the reservoir, multiple pump actuators formed on the first side of the substrate and positioned adjacent to the microtube at discrete, spaced positions along the length of the microtube, each pump actuator comprising a solid actuation member that is configured to expand when actuated, and a microcontroller provided on the second side of the circuit board, the microcontroller being configured to control actuation of the pump actuators; and
sequentially actuating the pump actuators under the control of the microcontroller so as to cause their actuation members to sequentially expand and sequentially compress the microtube to create peristaltic action that drives the fluid contained in the reservoir along the length of the tube and to the target site.

* * * * *